United States Patent [19]

Ratfisch

[11] Patent Number: 4,896,526

[45] Date of Patent: Jan. 30, 1990

[54] CONTINUOUS MONITORING OF A GAS MIXTURE

[76] Inventor: Werner Ratfisch, Martin-Luther-Strasse 1, 8000 München, Fed. Rep. of Germany

[21] Appl. No.: 201,558

[22] Filed: Jun. 2, 1988

[30] Foreign Application Priority Data

Jun. 9, 1987 [DE] Fed. Rep. of Germany ....... 3719231

[51] Int. Cl.⁴ ............................................. G01N 31/00
[52] U.S. Cl. ....................................... 73/1 G; 340/632
[58] Field of Search ............... 73/1 G, 863.31, 864.81; 340/632–634

[56] References Cited

U.S. PATENT DOCUMENTS

| | | | |
|---|---|---|---|
| 3,924,442 | 12/1975 | Kerho et al. | 73/1 G |
| 4,069,018 | 1/1978 | Karna et al. | 340/632 |
| 4,088,986 | 5/1978 | Boucher | 340/628 |
| 4,150,495 | 4/1979 | Stern | 73/1 G |
| 4,364,032 | 12/1982 | Narato et al. | 340/584 |
| 4,390,869 | 6/1983 | Christen et al. | 340/634 |
| 4,555,930 | 12/1985 | Leach et al. | 73/1 G |
| 4,565,086 | 1/1986 | Orr, Jr. | 73/23 |
| 4,578,986 | 4/1986 | Navarre | 73/1 G |
| 4,618,855 | 10/1986 | Hurdling et al. | 340/632 |
| 4,630,038 | 12/1986 | Jordan | 73/1 G |

*Primary Examiner*—Robert R. Raevis
*Attorney, Agent, or Firm*—Henry M. Feiereisen

[57] ABSTRACT

A method and an apparatus for the continuous monitoring of a gas mixture which contains explosive gases, for example in drying furnaces of painting or coating plants, with the concentration of the gas mixture being at an adequate distance from the so-called lower explosion limit includes the monitoring by means of flame ionization detectors. On occurrence of a fault an alarm display is actuated and firstly the respective flame ionization detector itself is checked and if necessary recalibrated. If the alarm persists after this recalibration, suitable steps must be taken in the plant itself, for example fresh air can be blown into the plant or the latter can be shut off.

8 Claims, 1 Drawing Sheet

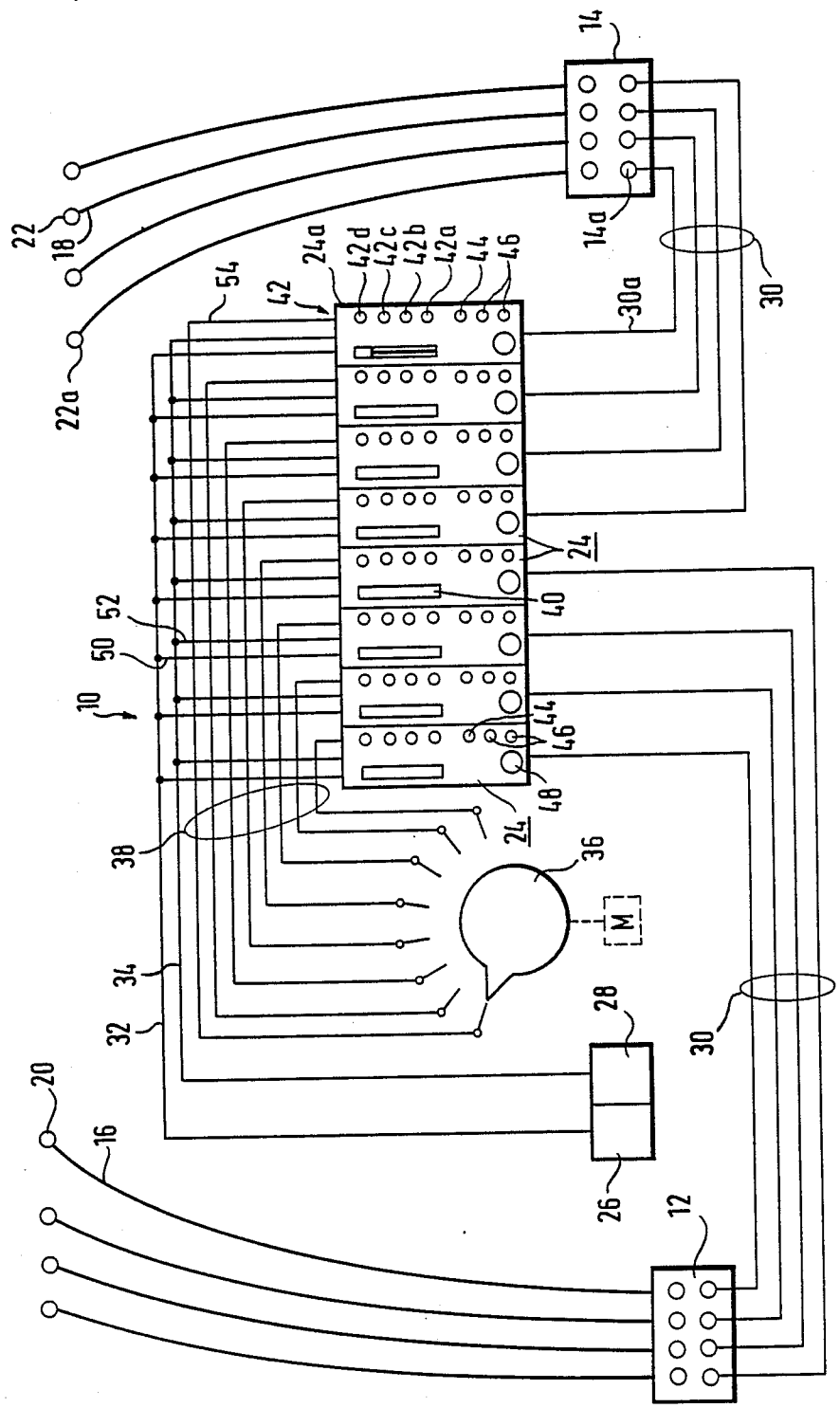

4,896,526

CONTINUOUS MONITORING OF A GAS MIXTURE

BACKGROUND OF THE INVENTION

The invention relates to a method for the 'continuous monitoring of a gas mixture,' in particular a mixture of hydrocarbon and air, by means of flame ionization, for example in painting plants and coating plants, in which at a plurality of spatially separate points of the plant gas samples are continuously withdrawn and are supplied to a flame ionization detector and associated with each withdrawal point is an ionization detector which is controlled by a programmer which is provided with an alarm means which responds on occurrence of a fault.

The use of flame ionization and the use of flame ionization detectors, hereinafter referred to as FIDs, for measuring and investigating gas mixtures is known.

With the FID the total concentration of the hydrocarbons is determined whilst the concentration of the individual components of the gas mixture is determined by means of gas chromatographs.

Gas mixtures, for example in painting plants or coating plants, contain various components which can be highly explosive.

For example, in the electrical industry wires are coated with insulating materials, in the furniture industry chip boards are provided with veneers and in the construction industry structural slabs or beams are coated with plastics; the same applies to the packaging industry in which webs of a support material are laminated with plastic layers.

Common to all these methods is that the coated materials or workpieces are led through drying apparatuses in which the solvents used in the coating must emerge in vapour form in the drying operation and be led off.

As already mentioned, these solvent vapours may be highly explosive and as a rule they are conducted to an afterburning apparatus and there burnt or supplied to a solvent recovery apparatus.

It must be ensured that these solvent vapours do not ignite themselves, which can lead to serious explosions and destruction of the entire plant, and that their concentrations remain adequately far from their so-called lower explosion limit.

Now, in such a drying apparatus at a plurality of measuring points gas samples are withdrawn and their concentration determined by means of FIDs, an FID being associated with each withdrawal point and each FID being controlled by a program generator, also referred to as a programmer.

The programmer is provided with an alarm means which responds on occurrence of a fault within the part of the plant monitored by said means.

Such a fault can occur in the monitored measuring point but also in the FID itself.

SUMMARY OF THE INVENTION

The invention is therefore based on the problem of further developing the method mentioned at the beginning in such a manner that on occurrence of a fault the location at which the fault occurs and possibly also the nature of the fault can be determined as rapidly as possible.

According to the invention this is achieved in that on occurrence of an alarm at one of the programmers firstly the associated FID is checked for functionability and if defective readjusted and that then if the alarm persists if necessary the plant is slowed down or switched off.

Expediently, after the adjustment of the respective FID the gas sample supplied thereto is analyzed by means of a gas chromatograph and the concentration of the individual components of the gas mixture determined.

If the total concentration of the gas mixture or the concentration of a single component is too high the ventilation of the plant may for example be increased and/or air blown into the region of the measuring point.

Preferably, to check the functionability of the FID at which the alarm has occurred the sample gas supply to said FID is switched off and the calibration checked, whereupon if necessary by supplying calibration gas said FID is recalibrated, whereafter the sample gas supply is switched on again.

The switching of the respective FID to zero gas and the connection of the calibration gas supply can be done manually by means of a selection switch which connects the respective FID to the calibration gas plant.

According to a further development of the invention it is further proposed in advantageous manner to use a power-actuated selection switch via which automatically the individual FIDs are continuously and consecutively interrogated for functionability and recalibrated when necessary.

Continuously and consecutively, in alternate manner an FID is switched off, i.e. the supply of the gas to be investigated is interrupted and the zero position set, whereafter the FID is connected to the calibration gas apparatus and recalibrated and then the gas supply to said FID connected again.

This achieves that the FIDs are continuously calibrated and faults or alarms due to a change of the calibration point during operation are avoided.

Advantageously, each programmer is equipped with a plurality of alarm stages which can be displayed for example by lamps so that the alarm is divided, for example a preliminary alarm, a function alarm and a main alarm.

BRIEF DESCRIPTION OF THE DRAWING

An example of embodiment of the invention will be explained hereinafter with the aid of the drawings, the single FIGURE of which shows schematically an apparatus made up of a plurality of flame ionization detectors, gas chromatographs and programmers, for monitoring a plurality of measuring points, for example in a coating plant.

DETAILED DESCRIPTION OF THE PREFERRED EMBODIMENT

The apparatus 10 includes an analyzer 12 and an analyzer 14 each comprising in the example described four flame ionization detectors. Of course, depending on the plant to be monitored more or less analyzers can be provided with more or less FIDs.

Each of the four FIDs in each of the analyzers 12, 14 may be preceded by a gas chromatograph; alternatively, a gas chromatograph may be associated with the four FIDs and then alternately allocated or connected in front of the individual FIDs. From the analyzers 12, 14 flexible measuring lines or probes 16, 18 extend to the respective measuring points 20, 22 of the plant to be monitored, which is otherwise not illustrated.

Associated with each of the FIDs of the analyzers 12 and 14 is a measuring line 16 and 18 respectively and via said measuring lines the FIDs are supplied with samples of the gas mixture to be monitored which are withdrawn at the respective measuring points 20 and 22.

Since the probes 16, 18 consist of flexible lines of any desired length which are introduced into the plant to be monitored, for example a drying furnace, the measuring points can be individually selected and also modified or changed.

The analyzers 12, 14 are controlled by program generators or programmers 24, with each FID being associated to one such programmer 24; in the example of embodiment illustrated the individual FIDs of the analyzers 12, 14 are connected via lines 30 to their respective programmer 24.

A calibration gas apparatus 26 is connected via a line 32 and branch lines 50 branching thereoff to each of the programmers 24. For example, calibration is attained by inserting one or more hydrocarbons of known composition through the flame so as to define upper and lower calibration limits within which each FID operates accurately. Furthermore, a zero point device 28, i.e. a device for checking and adjusting the zero point, is connected via a line 34 and branch lines 52 branching thereoff to each of the programmers 24. The zero point adjustment is attained e.g. by introducing a neutral gas through the flame of the respective FID.

Finally, selection switch 36 is provided which is manually actuable or automatically actuable with the aid of a motor M as indicated in broken lines, and connected via lines 38 to each of the programmers 24.

Each of the programmers is provided with a display means 40 for displaying the value measured by the associated FID and also with alarm indication lamps 42 which light up when a fault occurs.

Each programmer 24 can further be provided with a display lamp 44 for displaying the zero point which defines the point at which no hydrocarbons are burnt and with display lamps 46 for displaying the calibration limits within which each FID has to operate in order to deliver accurate values. In the nonlimiting example as illustrated in the FIGURE, a surpassing of the upper and lower calibration limits is indicated by the respective display lamps 46 A quality control lamp 48 is additionally provided to indicate when the gas to be checked reaches a predetermined total hydrocarbon concentration.

With reference to the apparatus 10 the execution of the method according to the invention will now be described.

If for example one of the FIDs, such as FID 14a in the analyzer 14 and associated to programmer 24a, shows an unexpected jump in the hydrocarbon concentration, one of the four alarm lamps 42, that is the lowermost alarm lamp 42a illuminates to provide a further signal informing an operator that an increase of the hydrocarbon concentration occurred which indicates some kind of fault in the system. The use of four alarm lamps 42a, 42b, 42c, 42d allows a gradation of alarm phases. Illumination of the lowermost alarm lamp 42a indicates a fault in the system of not yet dangerous proportions. With each subsequent activation of the other alarm lamps 42b, 42c, 42d, the danger of explosion increases due to increased hydrocarbon concentration.

After activation of the lowermost alarm lamp 42a, it is now first investigated whether the fault lies in the FID itself and for this purpose the FID 14a associated with the programmer 24a is connected via the line 30a and the programmer 24a and via the lines 54 and 38 and via the selection switch 36 as well as via the associated lines 34, 52 to the zero point setting 28. As previously set forth, the zero setting is carried out by introducing a neutral gas through the flame of the concerned FID, that is FID 14a. If the FID 14a operates correctly, the display should be at zero. Otherwise, the FID should be reset to zero.

This firstly interrupts the gas supply to the FID 14a and checks whether the FID 14a is correctly adjusted to the zero point. If such is not the case, the zero point setting can be corrected by means of the zero point setting means 28 and this can be checked for example by the zero point display lamp 44.

Thereafter the gas supply of the FID 14a can be switched on again. Conveniently, however, following the zero points setting the FID 14a is connected as before via the programmer and the selection switch 36, but this time via the lines 50, 32, to the calibration means 26 and it is checked whether the FID 14a is properly calibrated. If such is not the case, the FID 14a is recalibrated by means of the calibration means 26; the calibration setting or the upper and lower calibration limits can be checked with the aid of the calibration point display lamps 46.

The gas supply to the FID 14a is now switched on again. If the lamp 42a now goes out the fault was in the FID itself. If however the lamp does not go out and further lamps 42b, 42c, 42d are activated to thereby indicate higher alarm stages, for example a function alarm and a main alarm, the fault is in the measuring point 22a associated with the FID 14a.

The total concentration here of hydrocarbons may be too high or the concentration of the individual component may be too high.

The total concentration of hydrocarbons can be displayed for example by the display means 40 of each programmer but the display itself may be defective.

If therefore after the recalibration of the respective FID the alarm persists this means that something has changed at the respective measuring point, i.e. the total concentration of the hydrocarbons or the concentration of an individual component is closer or too close to the lower explosion limit.

With the aid of the alarm display lamps 42 gradations may be effected so that by an increasing number of lamps coming on it is indicated that the respective concentration is moving increasingly closer to the lower explosion limit.

It is now necessary to take suitable steps in the plant concerned, for example the drying apparatus, in order to prevent dangerous developments.

These steps may reside in that firstly the ventilation in the drying plant is increased; or in the region of the respective measuring point 22a fresh air may be blown in or the throughflow velocity of the material to be dried may be reduced or the plant shut down completely.

The individual steps may be combined as necessary.

To clarify more exactly whether the total concentration of the hydrocarbons or the concentration of an individual component is high or too high the gas chromatograph preceding the respective FID and also installed in the analyzer may be connected and as a result within 1-2 min an analysis of the gas mixture at the respective point is obtained.

To avoid the zero point setting and the recalibration in the event of a fault or indication of danger, expediently the selection switch 36 can be continuously power driven so that alternately and consecutively it couples one of the programmers or the associated FID to the zero point setting 28 and the calibration means 26 so that the FIDs of the analyzers 12 and 14 are recalibrated when necessary and thus continuously held correctly calibrated.

As already mentioned, with the display means 40 the total concentration and also the calibration setting can be displayed. The quality control lamp 48 lights up for example when a predetermined hydrocarbon concentration is reached or when a predetermined ratio of the concentrations of the hydrocarbon individual components with respect to each other is reached, it being possible to adjust the respective values.

The invention thus permits a central monitoring of the individual measuring points and also permits a total overview of the monitoring network of a production plant.

I claim:

1. A method for the continuous monitoring of a gas mixture, such as a gas mixture of hydrocarbon and air in a plant, comprising the steps of:
    withdrawing test samples of the gas mixture from a plurality of spaced withdrawal points of the plant and supplying the test samples to an associated flame ionization detector for analyzing the gas mixture, with each withdrawal point being operatively connected to such a flame ionization detector; and
    testing the operativeness of the flame ionization detectors by selectively connecting each flame ionization detector with a readjusting unit for allowing selective and separate testing of the operativeness of each flame ionization detector.

2. A method as defined in claim 1 wherein upon occurrence of a fault at one of the flame ionization detectors and indicated through triggering of an associated alarm signal said testing step includes discontinuing withdrawal of test samples and selectively checking the zero point and calibration of said flame ionization detector before manipulating the plant itself.

3. A method as defined in claim 1 wherein said testing step includes continuously checking the operativeness of the flame ionization detectors by automatically and consecutively connecting each flame ionization detector with the readjusting unit during operation of the plant.

4. Apparatus for the continuous monitoring of a gas mixture, such as a gas mixture of hydrocarbon and air in a plant, comprising:
    sampling means for withdrawing test samples of the gas mixture from a plurality of spaced withdrawal points of the plant;
    detector means for analyzing the test samples of the gas mixture, said detector means including a plurality of flame ionization detectors, with each withdrawal point associated to one flame ionization detector;
    adjusting means for allowing readjustment of said flame ionization detectors to their desired setting; and
    selector means including a selection switch which selectively connects each flame ionization detector with said adjusting means for allowing selective and separate testing of the operativeness of each flame ionization detector.

5. Apparatus as defined in claim 4 wherein said selection switch is a manually operated selection switch which upon occurrence of a fault indicated at one of the flame ionization detectors allows a connection of said one flame ionization detector with said adjusting means for selectively checking the zero point and calibration of said one flame ionization detector before manipulating the plant itself.

6. Apparatus as defined in claim 4 wherein said selection switch is a power-operated selection switch which automatically connects each flame ionization detector consecutively with said adjusting means for continuously checking the operativeness of the flame ionization detectors during operation of the plant.

7. Apparatus as defined in claim 4 wherein said adjusting means includes a zero point device for allowing zero point adjustment of the flame ionization detectors and a calibration device for allowing calibration of the flame ionization detectors.

8. Apparatus as defined in claim 4 wherein said detector means further includes alarm signals defining a plurality of alarm phases representing increasing stages of danger.

* * * * *